United States Patent [19]
Kimball et al.

[11] Patent Number: 5,146,432
[45] Date of Patent: Sep. 8, 1992

[54] METHOD FOR MAKING CEMENT IMPEDANCE MEASUREMENTS WITH CHARACTERIZED TRANSDUCER

[75] Inventors: Christopher V. Kimball, West Redding, Conn.; Sevig Ayter, Cupertino, Calif.

[73] Assignee: Schlumberger Technology Corporation, New York, N.Y.

[21] Appl. No.: 740,530

[22] Filed: Aug. 5, 1991

[51] Int. Cl.$^5$ ............................................. H04B 17/00
[52] U.S. Cl. ......................................... 367/13; 367/35
[58] Field of Search .................. 367/13, 35; 73/1 DV; 181/105

[56] References Cited

U.S. PATENT DOCUMENTS

| | | | |
|---|---|---|---|
| 4,255,798 | 4/1981 | Havira | 367/35 |
| 4,928,267 | 5/1990 | Kimbell et al. | 367/35 |
| 4,970,695 | 11/1990 | Huau | 367/13 |

OTHER PUBLICATIONS

"Transducer effects in acoustic Scattering measurements" by Johnson & Devaney, Appl. Phys. Lett. vol. 41, No. 7, Oct. 1, 1982, pp. 622-624.

"Quantitative investigation of disk ultrasonic sources" by Andow et al., J. Acoustic Soc. Am. 78, Nov. 85, pp. 1519-1529.

"Mathematical model for internal ultrasonic inspection of cylindrially layered structures" by Randel et al., J. Acoustic Soc. Am 83 Apr. 1988, pp. 1295-1305.

*Primary Examiner*—Daniel T. Pihulic
*Attorney, Agent, or Firm*—Marc D. Foodman; David P. Gordon

[57] ABSTRACT

Methods for characterizing acoustic transducers and using a characterized acoustic transducer for measuring cement impedance of a cased well are disclosed. The method for characterizing the acoustic transducer generally comprises: arranging the acoustic transducer a predetermined distance from a calibration target of known thickness; transmitting a pulse from the acoustic transducer through a known medium and toward the calibration target and measuring a return signal received therefrom; and fitting, via minimization, a return signal calculation generated by a model of the return signal which has a limited number of parameters, to the received return signal to determine a value for at least one of the parameters and thereby characterize the transducer. The preferred parameters for characterization are the transducer radius and stand-off, such that the transducer may be characterized as having an effective stand-off and an effective radius. The method for measuring cement impedance behind the casing in a well utilizes the method for characterizing the transducer, where the calibration target is preferbly of the same radius and thickness as the casing of the well. Then, downhole, a pulse is transmitted toward the casing in the well and the return signal is measured. Using the effective stand-off and effective radius previously determined as fixed values, the model of the return signal, which utilizes reflective coefficients which, inter alia, are a function of the cement impedance, is fit to the actual return signal to determine an indication of the cement impedance.

57 Claims, 6 Drawing Sheets

METHOD FOR MAKING CEMENT IMPEDANCE MEASUREMENTS WITH CHARACTERIZED TRANSDUCER

BACKGROUND OF THE INVENTION

1. Technical Field

The present invention is broadly directed to the characterization of transducers and the use of a characterized transducer in the investigation of materials. More particularly, the present invention is directed to using a characterized transducer in the measurement of the impudence of cement located behind a section of casing in a borehole.

Characterization of transducers is important in applications of ultrasonic technology. Manufacturers of transducers typically specify various characteristics of their transducers, including the center frequency and bandwith of the transducers which describes the time response of the transducer, and the f number, focal length, or transducer radius which describe the acoustic field of the transducer in space. As used in the art, the term "radius" refers to the radius of the electrode of the piezoelectric transducer which frequently is also the radius of the piezoelectric ceramic portion of the transducer.

Another spatial field characteristic of transducers is known in the art as "standoff". By exciting a transducer with an impulse response and analyzing the return signal as reflected off a reflector, the transducer's frequency characteristics are determined. Standoff refers to the spacing between the transducer and the reflector when the transducer is tested in this pulse-echo manner.

As used herein, "effective radius" refers to the dispersion of acoustic energy from the transducer being characterized; and more particularly to the radius of a well-defined transducer which would produce nearly the same spatial acoustic field as that of the transducer being characterized. A relatively small effective radius corresponds to an acoustic field that has energy distributed over a wide range of wavenumbers. Conversely, a relatively large effective radius corresponds to a transducer having energy distributed over a relatively narrower range of wavenumber.

Additionally, as used herein, "effective standoff" refers to the shape of the wavefronts generated by the transducer upon excitation; and more particularly to the standoff of a well-defined transducer which would produce nearly the same spatial field as that for the transducer being characterized. The effective standoff indicates the phasing of the transducer acoustic field at different wavenumbers. A relatively small effective standoff corresponds to an acoustic field having a relatively small radius of curvature in space of equal phase points. Conversely, a relatively large effective standoff corresponds to an acoustic field in which the equal phase points have a relatively large radius of curvature.

2. The State of the Art

In a typical wellbore application, cement is placed between the subsurface formation exposed by a borehole and a casing placed therein. The cement hydraulically isolates the different zones, e.g. water, oil, and gas, which may be located in the subsurface formation. Without a cement seal, the fluids under pressure in one zone may flow between the borehole and the casing to other zones. Thus, production zones could become contaminated, or the fluid of interest could escape from the zone determined for production, thereby rendering production uneconomical. Accordingly, it is imperative that there be a good cement seal; i.e. high cement quality between the formation and casing.

Defects in cement quality include annuli, channels, as well as complete voids in the cement. Defects in cement quality can also occur due to improper hardening of the cement, e.g., due to an improper amount of water in the cement mixture. Defects in cement quality can also occur during the life of the well such as due to corrosion of the casing. Once casing is installed in a well, it is at best difficult to remove for above-ground inspection. Thus it is desirable to be able to check the cement quality of the casing in situ.

Techniques for determining the cement quality of situ are well known. For example, U.S. Pat. No. 4,255,798 to Havira, and assigned to the same assignee as the present invention, which patent is hereby incorporated by reference herein, employs an acoustic pulse-echo technique having either a single transducer capable of directing its pulse at various azimuths or a plurality of transducers azimuthally located about a tool. The transducer transmits a pulse towards the casing and receives the return signal therefrom. The received signal includes an initial reflection segment which results largely from the reflection of the pulse off the inner surface of the casing, and a reverberation segment which results largely from the subsequent reverberations of the resonating casing section. The reverberation segment is indicative of the energy of the echo produced by the casing-cement interface.

In the preferred embodiment of the Havira patent, the initial reflection segment and the reverberation segment are processed separately. The entire initial reflection segment is selected to determined the peak value thereof. Thereafter, a predetermined portion of the reverberation segment is selected, allowing the energy of the reverberation segment to be calculated by an integrator. The calculated reverberation segment energy is divided by the peak value to generate a normalized cement quality signal.

It is has been found that the wideband signal processing with fixed time windows which is utilized in the Havira patent leads to several inaccuracies in the determination of cement quality. For example, inaccuracies are introduced due to the inclusion of unwanted noise components and phase variation between resonances, as well as due to the fact that the temporal portion of the reverberation segment signal indicative of cement quality varies with casing thickness. Additionally, it has been found that the information indicative of cement quality is located in a narrow frequency band about the frequency of the casing's thickness resonance in the reverberation segment. The narrow frequency band varies according to casing thickness.

U.S. Pat. No. 4,928,269 issued to Kimball, et al., assigned to the same assignee hereof, and hereby incorporated by reference herein, teaches a technique for determining the cement quality in situ wherein the problems inherent with wideband signal processing and fixed time windows are obviated. Specifically, the return waveform is analyzed to determine the casing thickness resonance frequency, and the return waveform is bandpass filtered about the determined thickness resonance frequency to the substantial exclusion of other thickness resonances. After time windowing a portion of the reverberation segment based on the casing thickness resonant frequency, the energy content therein is calculated.

In the Kimball et al. patent, a portion of the initial reflection segment is also time windowed, and the energy content therein is calculated. This energy calculation, representative of the energy of the acoustic reflection from the inner surface of the casing section is used to normalize the cementation signal calculated from the reverberation segment. Further, a calibration signal, commonly referred to as the free-pipe value, is determined by firing a transducer in pulse-echo fashion towards a casing, except that the impedance of the material behind the section of casing is known. After taking the difference between the normalized cementation signal and the normalized calibration signal, the impedance of the cement behind the casing is determined. By comparing the value of the impedance to predetermined impedance values indicative of good and bad cement quality, the cement quality can be determined.

It is known in the art that the particulars of the waveform returning from the casing as a result of an acoustic transducer pulse are a function of several factors, including transducer parameters. Various models which approximate the waveform as a function of the factors and parameters have been proposed. One of those models assumes that the transducer acoustic field has a single plane wave oriented at normal incidence to a planar reflecting surface. It is well known, however, that the normal incidence planar model doe not accurately describe the response as seen by the transducer. See e.g. Johnson, R. K. and Devaney, A. J. "Transducer Effects in Acoustic Scattering Measurements," 41 *Applied Physics Letters*, 622–24 (October, 1982), which is hereby incorporated by reference herein. These inaccuracies are evident in differences between waveforms from the normal incidence planar model and those obtained experimentally. Without calibration, the techniques disclosed in U.S. Pat. Nos. 4,255,798 and 4,928,269 which are based on the normal incidence planar model can be off by as much as 1 MegaRayl (MRayl). A 1 MRayl cement impedance error can be important, particularly when modern light-weight cements are in use.

A second model which better approximates the return waveform is set forth the in the aforementioned article by Johnson and Devaney. The "Johnson-Devaney" model equates the return waveform $V(f)$ according to:

$$V(f) = \int_0^{\pi/2} W(f,\theta) R(f,\theta|z) d\theta \quad (1)$$

where $W(f,\theta)$ is a kernel, and $R(f,\theta|z)$ are reflection coefficients of the target. The Johnson-Devaney model assumes that the transducer is circularly symmetric and that the target is a flat surface. Thus, even if Johnson and Devaney had provided a method for utilizing their model to obtain measurements of cement impedance (which they did not), the model would have inaccuracies due to the fact that the reflective surface downhole is a casing which is curved.

A third model for approximating a return waveform is set forth in C. J. Randall, and F. E. Stanke, "Mathematical Model for Ultransonic, Internal Inspection of Cylindrically Layered Structures", *J. Acoustical Soc. Am.* 83; pp. 1295–1305 (1988), which develops a complex equation for the waveform received by an irregular transducer as a result of a reflection from a curved surface. In the Randall-Stanke model, the return wave is a function of the casing diameter, transducer parameters such as length and apodization, and stand-off between the transducer and the target. While the Randall-Stanke model is theoretically a very good approximation, the calculation time per waveform is very large. Also, the large number of unknown parameters makes an inversion difficult, as a search over many possible alternative parameter values would be required. Thus, the Randall-Stanke model is not particularly useful in developing a solution to the forward problem of finding cement impedance.

SUMMARY OF THE INVENTION

It is therefore an object of the invention to determine effective parameters of an acoustic transducer which characterize its spatial acoustic field.

It is another object of the invention to determine the impedance of cement behind a casing via use of a transducer having effective parameters determined in a characterization procedure.

It is a further object of the invention to determine the impedance of cement behind a casing by fitting a model of the response waveform to the actual return signal, where the fitting error between the model response waveform and actual return signal is a quantitative quality indicator of the impedance determination.

It is yet another object of the invention to determine the impedance of cement behind a casing by fitting a model of the casing environment to the actual return signal, wherein the model utilizes the effective parameters of a transducer for the particular casing curvature and thickness, and wherein the effective parameters are known as a result of a characterization procedure.

In accord with the objects of the invention, the method of measuring cement impedance of a cased well of known diameter with a tool having an acoustic transducer, generally comprises: characterizing the acoustic transducer by testing the acoustic transducer relative to a calibration target having a diameter and thickness substantially equal to the diameter and thickness of the casing of the well, and characterizing the acoustic transducer as having an effective radius ($a_e$), and an effective stand-off ($S_e$); transmitting a pulse from the acoustic transducer toward the casing in the well and measuring the return signal therefrom; and fitting a model of the return signal to an actual return signal to determine an indication of the cement impedance, where the model of the return signal utilizes the effective radius and the effective stand-off of the acoustic transducer as determined during the characterizing step.

A preferred manner of characterizing the acoustic transducer includes a precharacterization uphole, and additional characterization downhole. Uphole, the transducer is arranged to emit an uphole test pulse toward a surface which is similar to the expected downhole casing, and to detect an uphole test return signal. A model of the return signal which includes an unknown effective transducer radius and an unknown effective transducer standoff is fitted to the uphole test return signal by varying the unknowns. Then, having preliminary determinations of the effective transducer radius and standoff, additional characterization is done downhole at the site of interest by providing the logging tool with a target which has a similar thickness and radius as the casing. Characterization proceeds by arranging the transducer to emit a downhole test or calibration pulse toward the logging tool target and detecting a downhole test or calibration return signal, and then fitting the model of the return signal to the downhole calibration return signal. The fitting procedure for the downhole test pulse may determine values for the mud impedance as well as a narrow range of values for the effective radius and effective standoff of the transducer as the uphole precharacterization will have already identified expected effective radius and effective standoff values. The mud impedance thus determined can be used in the cement impedance measurement and for other purposes.

An additional preferred aspect of the invention includes the use of a modified Johnson-Devaney model for modeling the return signal from a curved surface, where effective radius and effective standoff values are utilized in lieu of radius and standoff values, with the effective radius and effective standoff values being functions of the particular curvature of the surface involved and the actual standoff.

Additional objects and advantages of the invention will become apparent to those skilled in the art upon reference to the detailed description in conjunction with the accompanying drawings.

DETAILED DESCRIPTION OF THE PREFERRED EMBODIMENTS

Figure 1:
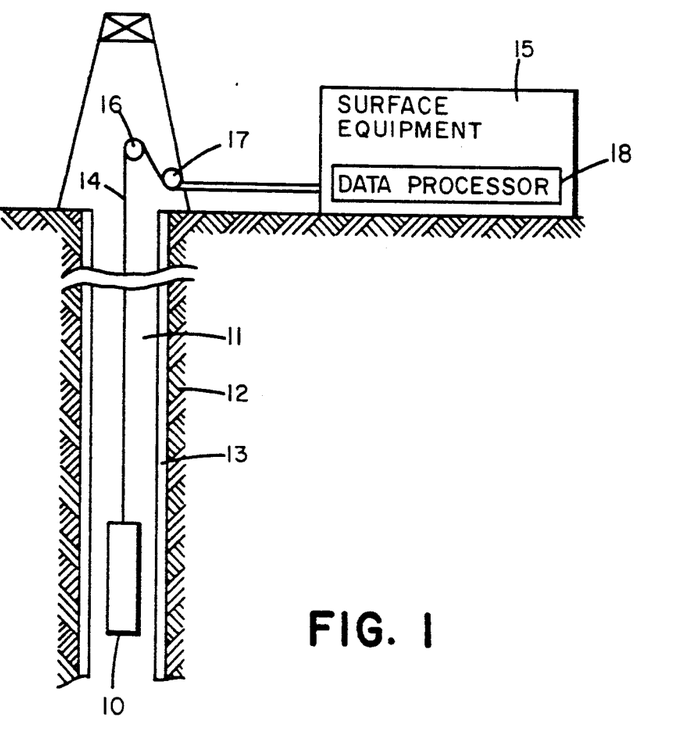
FIG. 1 is a schematic diagram of a borehole logging operation in which the present invention may be advantageously employed.

A schematic diagram of a logging operation is shown in FIG. 1. A tool, or sonde, 10 for evaluating cement quality is located in a cased borehole 11 penetrating an earth formation 12. To prevent fluid communication between otherwise isolated zones in the formation, cement (not shown) is placed in the annulus (not shown) between casing 13 and the borehole wall. The sonde is preferably lowered into the cased borehole by an armored multiconductor cable 14 and slowly raised by surface equipment 15 over sheave wheel 16, while cement quality measurements are performed. The depth of the sonde in the cased borehole is measured by depth gauge 17, which measured cable displacement.

Figure 5:
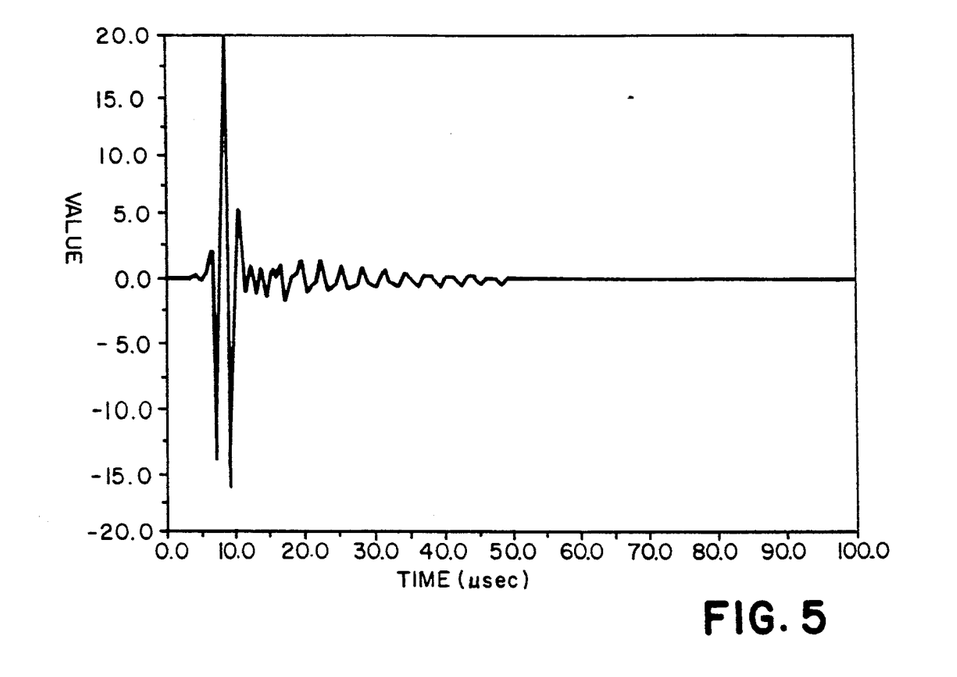
FIG. 5 is a return waveform received by a transducer from a 9 mm casing having a seven inch diameter in a freepipe condition.

In measuring cement quality, sonde 10 emits acoustic excitation pulses. Return waveforms, such as that of FIG. 5, are produced as a result of reflections of the emitted pulses from the casing, as well as from reverberations of the casing. The return waveforms can be analyzed by the sonde in situ, analyzed by data processor 18 at the surface, or stored, either in the sonde or at the surface, for analysis at a remote location. In the preferred embodiment, the return waveform data is transferred to data processor 18 by cable 14, where the cement quality can be determined.

The sonde 10 is capable of obtaining cement quality measurements azimuthally, and is preferably of the design described in U.S. Pat. No. 4,255,798 to Havira, which was previously incorporated by reference herein. Further, the sonde preferably includes apparatus as described in U.S. Pat. No. 4,970,695 to Huau, which is hereby incorporated by reference herein, to characterize the transducer of the sonde in situ.

Figure 2:
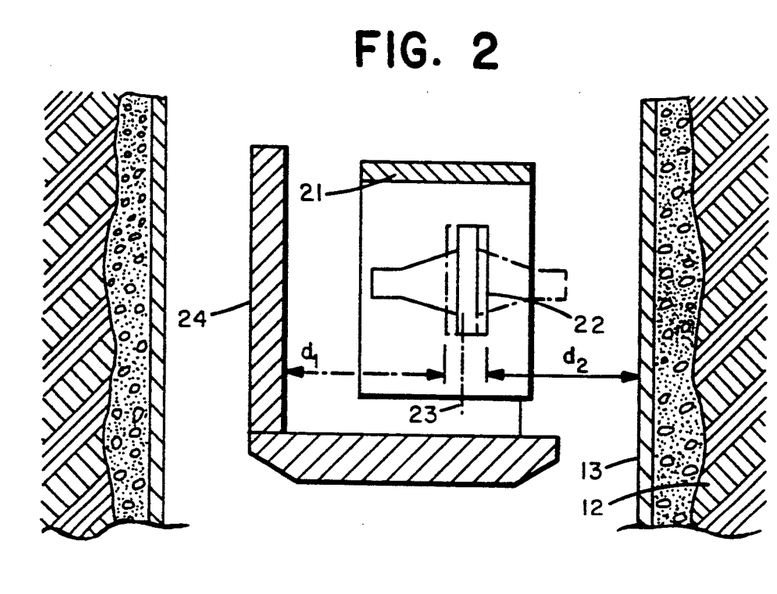
FIG. 2 illustrates a device for rotating a transducer for in situ transducer characterization and cement quality measurement.

As seen in FIG. 2, the in situ sensor calibrator of the present invention includes plate 21 for supporting transducer 22, and a mechanism (not shown) for rotating the transducer about axis 23. In characterization mode, as indicated in phantom, the transducer is rotated to face calibration target 24. The calibration target 24 is disposed parallel to the longitudinal axis of the sonde and is situated at the same level as the transducer 22. The calibration target is preferably chosen to have characteristics (parameters) which are substantially identical to those of the casing under investigation; e.g., the thickness and radius of curvature of the target is the same as the thickness and radius of curvature of the casing. In the preferred embodiment, the calibration target is an approximately sixty degree segment of four inch length casing whose parameters match the casing under investigation. In arranging the borehole tool and in conducting the characterization, the distance $d_1$ between the transducer and the calibration target in characterization mode (phantom indications of FIG. 2) is preferably substantially identical to distance $d_2$ between the transducer and the casing in measurement mode.

Before describing the methods utilized for finding the impedance of the cement behind the casing, a discussion is in order regarding the methods of the invention for characterizing the transducer, as well as the theoretical basis of the same. Using the aforementioned Johnson and Devaney article as a starting point, and as indicated above, the pulse-echo frequency response V(f) of a circularly symmetric reciprocal transducer, oriented perpendicular to isotropic planar layers, L, is defined as:

$$V(f) = \int_0^{\pi/2} W(f,\theta)R(f,\theta|L)d\theta \quad (2)$$

where $R(f,\theta|L)$ are the complex planar reflection coefficients for the layers, L, at frequency f, and incidence angle $\theta$, and where $W(f,\theta)$ is called the plane wave kernel. The plane wave kernel is defined according to:

$$W(f,\theta) = (2\pi/V_{fluid})|k|^2 \sin\theta\cos^2\theta A^2(f,\theta) \, e^{j2|k|S\cos\theta} T(f) \quad (3)$$

where $V_{fluid}$ and k are the velocity and wavenumber, respectively in the immersion fluid, $A(f,\theta)$ is the output acoustic response function of the transducer in frequency and incidence angle, S is the standoff or the distance from the transducer to the plate, T(f) is the spectrum of the electrical excitation, and $\theta$ is the angle relative to normal at which a plane wave impinges on the target plate.

With the pulse echo frequency response V(f) as defined, the Fourier transform of V(f) is v(t) and is called the "return signal". V(f) and v(t) as defined assume that the return signal consists of a single reflection from the target and excludes multiple reflections between the transducer and reflector by time gating, as is known in the art.

In order to characterize the transducer, and as described in greater detail hereinafter, the efforts of T(f) are removed by a process called whitening, and, in accord with a preferred embodiment of the invention, a particular model of the transducer is utilized so that A(f,$\theta$) depends on two parameters only; the effective radius, and the effective standoff. With certain environmental parameters such as borehole fluid speed known, and with complex planar reflection coefficients R(f,$\theta$) determinable as known in the art, given the two parameters, model waveforms can be generated pursuant to equation (2) in a process generically called a "forward model". Moreover, because the preferred model of the transducer utilizes only two transducer parameters, the best-fitting transducer parameters for an experimental waveform can be determined by an iterative process in a procedure generally called an "inverse model" as described in more detail hereinafter.

More particularly, in order to remove the electrical excitation frequency dependence T(f) from the kernel determination (and hence the response), the response may be "whitened" by several methods. The most accurate method is to examine the response of the transducer to a very thick (many wavelengths at the transducer center frequency) or so called "infinite" block or plate to obtain the received spectrum $V^\infty(f)$. In situations in which this target is impractical, a less accurate method known as auto-whitening can be use. In auto-whitening, the usual finite thickness target is used but the waveforms are truncated in time to exclude the late reflections. This truncation is achieved by applying either a rectangular or smooth window, i.e., Gaussin window, about the first reflection from the target, where the window is chosen to exclude or severely attenuate the late arrivals. The transform of this window then gives $V^\infty(f)$ for auto-whitening. It will be evident to those skilled in the art that the preferred whitened response $V^0(f)$, which is preferably set equal to the unwhitened response divided by the response of a two layer system (i.e., $V^0(f) = V(f)/V^\infty(f)$) is defined according to:

$$V^0(f) = \int_0^{\pi/2} W^0(f,\theta) R(f,\theta | L) d\theta \qquad (4)$$

where $W^0$ is the whitened kernel defined by $$W^0(f,\theta) = W(f,\theta)/V^{2B}(f) \qquad (5)$$

Thus, if the infinite plate response (i.e., the response of the two layer system) of a transducer is known, a whitened response can be constructed which depends only on the whitened kernel. It should be noted that because zeros in $V^{2B}(f)$ are possible, wherever $V^\infty(f)$ is more than say, 40 db below its maximum value, $V^0(f)$ is zeroed.

Because an infinite block waveform is difficult to obtain in situ in the cased borehole, auto-whitening is utilized in the preferred embodiment as discussed hereinafter. As aforementioned, auto-whitening comprises time windowing a plate response about its first arrival and using the Fourier transform of the windowed waveform for whitening.

A second preferred change to simplify a determination of A(f,$\theta$) is to assume that the transducer is a Gaussian apodized disk of radius a acting at a standoff S. The acoustic output response $A_{disk}(f,\theta)$ for a Gaussian-apodized disk of radius a is given by:

$$A_{disk}(f,\theta) = e^{-[(|k|\sin\theta\, a)^2]/2} \qquad (6)$$

The corresponding kernel for the Gaussian-apodized disk transducer at standoff S is given by $$W_{disk}(f,\theta) = (2\pi/V_{fluid})|k|^2 \sin\theta \cos^2\theta A^2(f,\theta)$$
$$e^{-(|k|\sin\theta a)^2} e^{j2|k|S\cos\theta} \qquad (7)$$

Utilizing relationships (7) and (4) above, the whitened waveform for the Gaussian-apodized disk is modeled according to:

$$V^0_{wideband}(f) = \int_0^{\pi/2} W^0_{disk}(f,\theta) R(f,\theta|L) d\theta$$

$W^0_{disk}(f,\theta)$ is obtained from relationships (7) and (5) above.

While the whitened wide-band response model for a Gaussian-apodized disk transducer can be utilized, a whitened bandpass approximation is preferred for the response of an apodized disk. There are two reasons for this. First, the numerical calculation of a whitened wideband model waveform over a discrete grid of numerous frequency points and incidence angles requires numerous calculations. Second, reducing the bandwidth of the measurement reduces the number of degrees of freedom in the response and thereby increases the possibility of a good fit.

More particularly, because the energetic portions of the late-time response are in a frequency band near a resonant frequency of the target, the bandpass approximation is centered on that resonant frequency. For example, the frequency of the n'th plate resonance for a plate of thickness d is given by:

$$f_n = n\, (v_p(\text{casing}))/2d \qquad (8B)$$

where $v_p(\text{casing})$ is the speed of compressional waves in the casing (i.e. steel). For the preferred embodiment of the invention, n is set to one (i.e., n=1). Consequently, quantity d specifies both the target plate thickness, and, through equation 8B, the center frequency of the bandpass approximation.

The whitened bandpass approximation for the response of an apodized disk can be written as:

$$V^0_{bp}(f,d) = \int_0^{\pi/2} W^0_{bp}(\theta,d) R_{bp}(f,\theta|L) d\theta \qquad (9)$$

where the whitened bandpass kernel $W^0_{bp}(\theta, d)$ is defined by:

$$W^0_{bp}(\theta,d) = C\sin\theta\cos^2\theta\, e^{-|k|^2 \sin^2\theta a^2}\, e^{j2kS(1-\cos\theta)} \qquad (10)$$

In equation (10), C is a complex scale factor which can be assumed to be constant in the approximation band centered at $f_1$. Also, in equation (10), k is the wavenumber in the fluid at the center frequency ($f_1 = v_p(\text{casing})/2d$) of the bandpass approximation. It will be appreciated by those skilled in the art that for a fixed plate thickness d, the whitened bandpass kernel $W^0_{bp}(\theta,d)$ is not a function of frequency. Also, it will be appreciated that the quantity S effects only the phase of $W^0_{bp}(\theta,d)$. As a result, a and S act as independent variables, which simplifies inversion.

Returning to the approximation of equation (9) of the response of the apodized disk, the reflection coefficients $R_{bp}(f,\theta|L)$ are defined by $$R_{bp}(f,\theta|L) = e^{j2\pi(f-f_1)S/V_{fluid}(1-\cos\theta)}R(f,\theta|L) \text{ if } f > 0; \quad (11)$$

$$e^{j2\pi(f+f_1)S/V_{fluid}(1-\cos\theta)}R(f,\theta|L) \text{ if } f < 0.$$

The planar refection coefficients are well-known at frequency f and incidence angle $\theta$ for a planar layering specified in terms of number of layers and specified in terms of the thickness, density, compressional and shear velocities of each layer. (See, L. M. Brekhosvskikh, *Waves in Layered Media;* Academic Press, New York (1980). A computer program which calculates the planar reflection coefficients is attached hereto as Appendix A.

Equation (11) indicates that the bandpass planar reflection coefficients are dependent on the standoff S. This dependence will be recognized as the introduction of a small variation (relative to $\theta=0$) of the group delay of plane waves for different incident angles, $\theta$. Those skilled in the art will appreciate that $R_{bp}(f,\theta|L)$ depends only weakly on S. Therefore, a good approximation for the bandpass planar reflection coefficients can be made:

$$R_{bp}(f,\theta|L) = e^{j2\pi(f-f_1)SG/V_{fluid}(1-\cos\theta)}R(f,\theta|L) \text{ if } f > 0; \quad (11A)$$

$$e^{j2\pi(f+f_1)SG/V_{fluid}(1-\cos\theta)}R(f,\theta|L) \text{ if } f < 0;$$

where SG is the standoff. For the model case of a Gaussian apodized disk over a plate, SG and S are equal. When fitting experimental data to the model, the parameters (a,S) in equation (10) are considered unknown, and the best-fitting values of (a,S) in equation (10) are called the "effective radius" ($a_e$) and the "effective standoff" ($S_e$). During the fitting process, SG is kept constant at the actual standoff of the transducer in the experiment.

The removal of SG from the fitting process over (a, S) allows $R_{bp}(f,\theta|L)$ to be precomputed. Since the planar reflection coefficients are computationally difficult, the approximation of equation (11A) greatly speeds up the calculations. This is seen by taking the inverse Fourier transform of equation (9):

$$V^0_{bp}(t) = \int W^0_{bp}(\theta,d) R_{bp}(t,\theta|L) d\theta \quad (11B)$$

Here $R_{bp}(t,\theta|L)$ is the inverse Fourier transform of $R_{bp}(f,\theta|L)$, which can be precomputed for a given SG. Equation (11B) shows that the whitened bandpass model response is simply a weighted (by $W^0_{bp}(\theta,d)$) integral of $R_{bp}(t,\theta|L)$. This integration involves new values only for the easily computed $W^0_{bp}(\theta,d)$ for each pair of transducer parameters (a,S).

Figure 3:
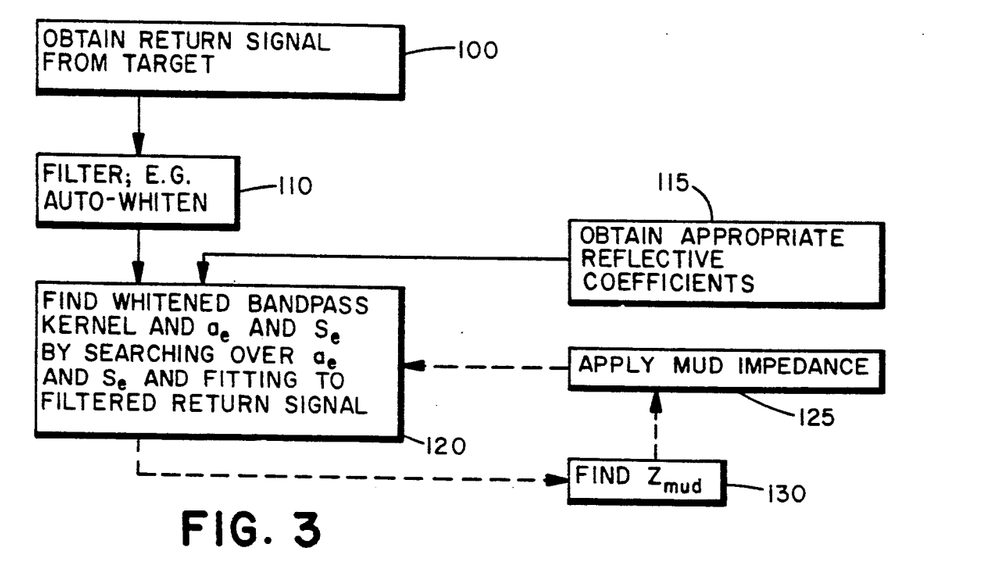
FIG. 3 is a flow chart of the preferred method for characterizing a transducer.

In practicing the preferred embodiment of the invention as illustrated in the flowchart format of FIG. 3, a transducer is characterized by first obtaining the return signal from a target at step 100, and auto-whitening the return signal at 110 as discussed above by time windowing and Fourier transforming. Knowing the auto-whitened return signal from step 110, and the bandpass reflection coefficients (which are obtained from texts or other sources at 115), the whitened bandpass waveform is found for any assumed (a,S) at 120 in accord with equations (7), (9) and (10). The effective transducer parameters ($a_e$, $S_e$) are then preferably found by searching over various values for the standoff and radius to find a best fit of the whitened bandpass waveform relative to the auto-whitened return signal in accord with a least mean squared technique.

While transducers can be usefully characterized as discussed above without requiring the many thousands of measurements required by the prior art (see, e.g., J. D. Aindow, et al., "Quantitative Investigation of Disk Ultrasonic Sources", *J. Acoust. Soc. Am.* 78 (5); Nov. 985 pp 1519–1529), those skilled in the art will appreciate that due to extreme pressures and temperatures, the cased borehole environment is different than the environment of the laboratory. Thus, it is desirable to characterize a transducer in situ, and to use the characterized transducer to find the impedance of the cement behind the casing.

Transducer characterization in situ proceeds essentially as discussed above and set forth in FIG. 3, except that the reflection coefficients R are chosen for a free-pipe arrangement where the target is surrounded by fluid. Also, the target used for the characterization down-hole is preferably a curved target which has the same radius and thickness as the casing to be investigated (as discussed above with reference to FIG. 2). It has been found by the inventors, that while the radius of the target and thickness will affect the effective standoff and effective radius, these measured values allow accurate prediction of the transducer response for targets of that radius and thickness. This ability to predict the response from the model is important to the determination of cement and mud impedance as described below.

With the inverse problem solved such that the transducer is characterized as having an effective standoff and an effective radius for a particular casing thickness and diameter, the problem of finding the cement impedance can be solved. As set forth in FIG. 4, a return signal from the casing itself is obtained at step 150 and filtered at 160 to preferably obtain an auto-whitened bandpass return signal. Since the effective standoff $S_e$ and effective radius $a_e$ are known in accord with the methods described with reference to FIG. 3, the bandpass kernel of equation (10) is known. With the auto-whitened bandpass return signal obtained at step 160, and a known bandpass kernel, what remains is to find bandpass reflection coefficients which provide a best fit between the auto-whitened bandpass return signal and the integral of the bandpass kernel times the bandpass reflection coefficients as they are theoretically related by equation (9). This is accomplished by varying the bandpass reflection coefficients at step 170 until an optimal fit is obtained; i.e., the error between the theoretical $V^0_{bp}(f,d)$ of equation (9) and the measured filtered signal of step 160 is minimized. Because the bandpass reflection coefficients $R_{bp}(f,\theta|L)$ are calculable and known to be functions of the cement impedance and the acoustic properties of the casing and borehole fluid (See I. M. Brekhosvskikh, *Waves in Layered Media;* Academic Press, New York (1980), the cement impedance at which the optimal fit occurs is taken as the determined impedance at step 190.

Restating the manner of solving for cement impedance in a slightly different way, with the inverse problem solved such that the transducer is characterized as having an effective standoff and an effective radius for a particular casing thickness and diameter, the forward model of equation (11B) can be applied to predict waveforms for situations with different reflection coefficients $R_{bp}(f,\theta|L)$, specifically for different layerings, L. As set forth in FIG. 4, a return signal from the casing itself is obtained at step 150 and filtered at 160 to preferably obtain an auto-whitened bandpass return signal. If it is considered that all characteristics of the layering L are known except for cement impedance, reasonable estimated values Z, for the cement impedance may be chosen, and bandpass reflection coefficients $R_{bp}(f,\theta)$ may then be calculated. Then, equation 11B is used to calculate the whitened, bandpass model waveform, using the previously determined effective radius and effective standoff. The whitened, bandpass model waveform can then be compared to the whitened, bandpass return signal, and the mean-squared error calculated at step 170. By searching over reasonable values of Z, a final impedance Z which substantially minimizes the error between the model waveform and return signal is taken as the measured cement impedance at step 190.

It will be appreciated by those skilled in the art that impedance (Z) is defined according to $Z=c\sigma$ where c is the velocity in the medium of interest, and $\sigma$ is the density. In determining reflection coefficients, each layer should be characterized by its velocity, density, and thickness. In water, the fluid shear velocity is typically taken as zero, and the density as one (gm/cc). In mud, the velocity can be determined by measurements well known to those skilled in the art, and the density can either be measured or determined as discussed in more detail hereinafter. For cement, the density is typically taken as 1.6 gm/cc. Thus, it reality, it is the velocity which is being measured by the acoustic tool and which is the factor which causes a change in impedance as determined by the invention.

Figure 4:
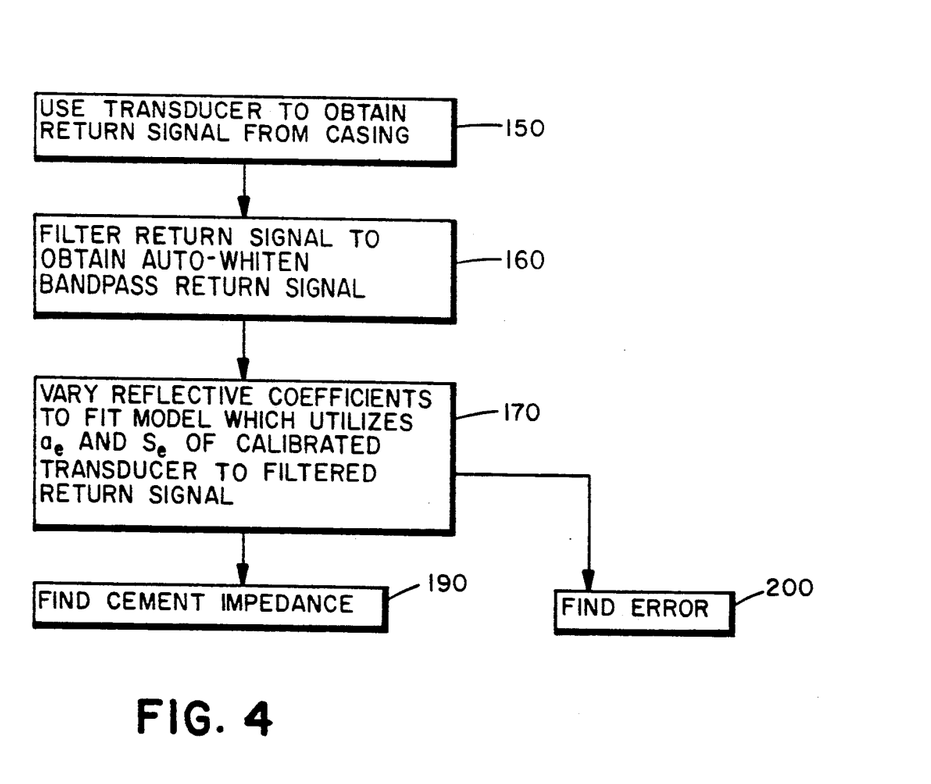
FIG. 4 is a flow chart of the preferred method of utilizing a characterized transducer to find cement impedance.

Besides finding the impedance of the cement layer behind the casing, in accord with another aspect of the invention, and as shown in FIG. 4 at step 200, the error in the fit between the received filtered signal and the modeled signal is output. This error provides an indication as to the reliability of the impedance determination.

More particularly, the preferred error metric utilized is the conventional mean-squared error metric. As indicated with reference to FIGS. 3 and 4, the received return signal is normalized via bandpass filtering prior to the mean-squared error calculation. Since the resonance effects of interest are narrowband and have a center frequency, f, which is easily estimated by a knowledge of the thickness of the casing, the resonances are compared in a band determined from the assumed casing thickness d. The data is considered in terms of its complex envelope v(t) at thickness d according to $$v(t,d)=2g(t,d) * [v(t) e^{-j2\pi ft}] \quad (12)$$

where v(t) is the Fourier transform of V(f) as discussed with reference to equation (2), and g(t,d) is the inverse Fourier transform of G(f,d) which is defined by $$G(f,d) = (1/\sqrt{2\pi Bf_1}) e^{-[f/Bf_1]^2/2} \text{ if } |f| < 4Bf_1 \text{ and 0 otherwise} \quad (13)$$

and with B being a bandwith factor (preferably equal to 1/16). The gain of the signal or its delay do not effect the shape of the whitened kernel and consequently the filtered waveforms are normalized by setting the total energy to a constant E*, where E* is defined by:

$$E^* = \int_{-\infty}^{+\infty} |v(t,d)|^2 dt \quad (14)$$

Normalization eliminates unnecessary factors and provides a standardized basis for viewing waveforms.

Given two waveforms $v_1(t,d)$ and $v_2(t,d)$ normalized as indicated above, then the error $\epsilon(d)$ between the two waveforms is defined as $$\epsilon(d) = 10\log\left[\min_{\phi}\left(\int_{-\infty}^{+\infty} |v_1(t,d) - v_2(t + \phi,d)|^2 dt\right)\right] \quad (15)$$

This is the usual mean-squared error metric with a minimization over time shift $\phi$ to eliminate the effects of small time misalignments. The error $\epsilon$ is expressed in decibels (dB) relative to the value one. Large negative values indicate good fits, while independent noise would provide a value of approximately 3 dB.

The mean-squared error $\epsilon(d)$ is sensitive to small (e.g., 0.01 mm) variations in casing thickness d. To ensure an accurate fitting of the waveforms, a search having fine granularity is preferably made over $\epsilon(d)$ for thicknesses in an interval about the specified casing thickness. Thus, the values of mean-squared error in the preferred embodiment represent minima over small time shifts and thickness variations.

In some situations, the impedance of the borehole fluid (mud) is unknown. Since the mud impedance is needed in the calculation of the refection coefficients (as mentioned above), and is of value to the other acoustic measurements, a determination of the mud impedance is desirable. In accord with another aspect of the invention, the mud impedance can be found as part of the process of finding the effective radius and effective standoff as discussed above with reference to FIG. 3. In particular, the downhole tool includes a target of known thickness and radius, with the mud being located at either side of the target. Given that the whitened waveform is obtained by measurement and filtering, a fit between the whitened waveform and a model of the waveform for plausible values of a, S, and $Z_{mud}$ (i.e., a three dimensional search) can be preformed to arrive at the effective radius, effective standoff, and mud impedance.

The preferred manner of conducting the three-dimensional search for a, S and $Z_{mud}$ according to the invention is to initially assume the mud impedance to be some reasonable value such as the impedance of water (as indicated at 125 of FIG. 3), and then to conduct a two-dimensional search to find interim effective radius and effective standoff values (as indicated at 120). With the interim values, a search is made over $Z_{mud}$ at 130 to find an interim $Z_{mud}$ value. The process iterates as indicated with additional searches for new effective radius and effective standoff values, and then with those new values, a new $Z_{mud}$ value until a good fit is found. In practice, it has been found that the transducer parameters are only weakly dependent on $Z_{mud}$, and hence few (one or two) iterations are required.

Turning to FIG. 5, a laboratory waveform is seen for a 9 mm casing having a 7-inch outer diameter and tested under freepipe (i.e., water on both sides of the casing) conditions. The waveform consists of a large pulse of the first reflection from the fluid/casing interface (inside face of casing) plus a decaying response due to resonances within the casing. The waveform of FIG. 5 is zeroed forth-five microseconds after the initial peak to eliminate secondary reflections in accord with the preferred embodiment of the invention.

Using the casing which provided the waveform of FIG. 5 and the transducer which detected the waveform, the transducer was characterized in the laboratory in accord with the teachings of the method invention. Using the inverse model, and applying the described methods (with the bandpass model implemented over a discrete grid in $(f,\theta)$, and with the incidence angle grid taken at 0.3° between 0° and 14.4° which is the critical angle of the water/steel interface), optimal effective radius values and optimal effective standoff values were found for the transducer as a function of assumed casing thickness. The results are plotted as FIGS. 6a and 6b. In addition, as seen in FIG. 6c, error values were plotted for how well the optimal effective radius and effective standoff values caused the model to fit to the obtained data. A review of FIG. 6c shows that the minimum error (i.e. the best fit) was obtained at a casing thickness of approximately 8.85 mm. As a result, for the particular casing under investigation, the transducer effective standoff and effective radius are those which were found for the 8.85 mm thickness; corresponding to an effective radius of 10.1 mm, and an effective standoff of 57.6 mm. Here SG was taken as 51 mm; the difference in group delay between that for SG and that for $S_e$ being negligible.

Figure 6A:
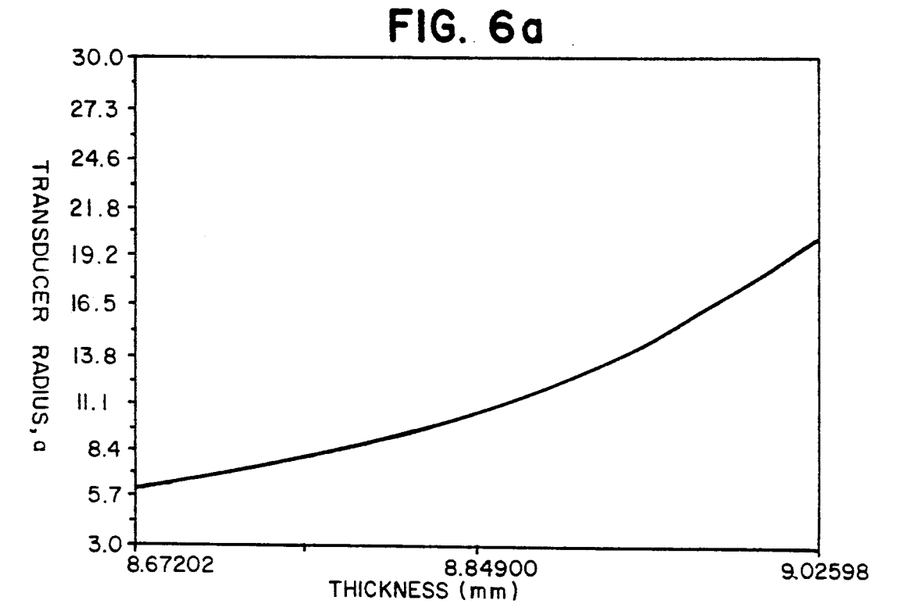
FIGS. 6a and 6b are graphs of the effective radius and effective standoff of the transducer receiving the return waveform of FIG. 5 versus the assumed thicknesses of the casing.
Figure 6B:
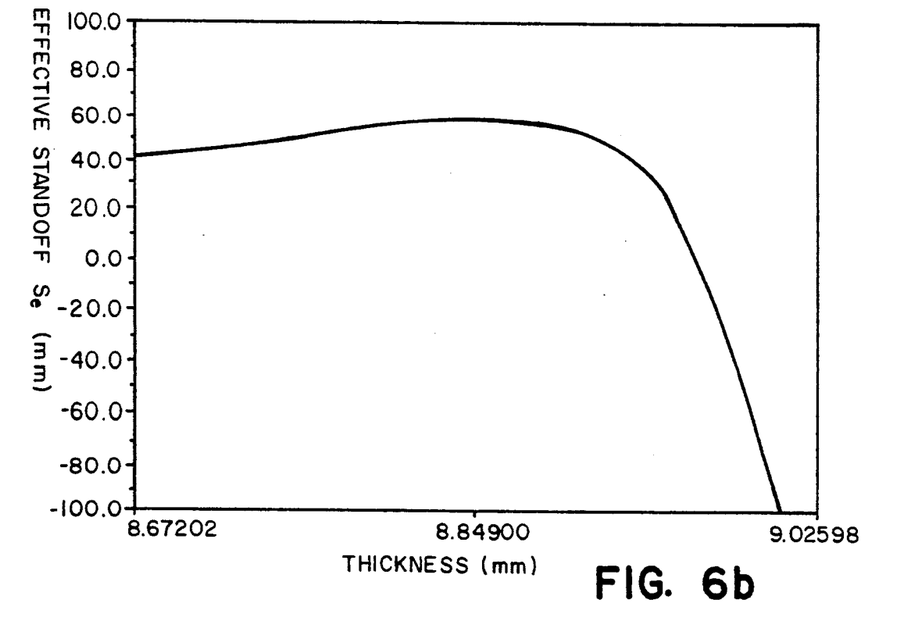
Figure 6C:
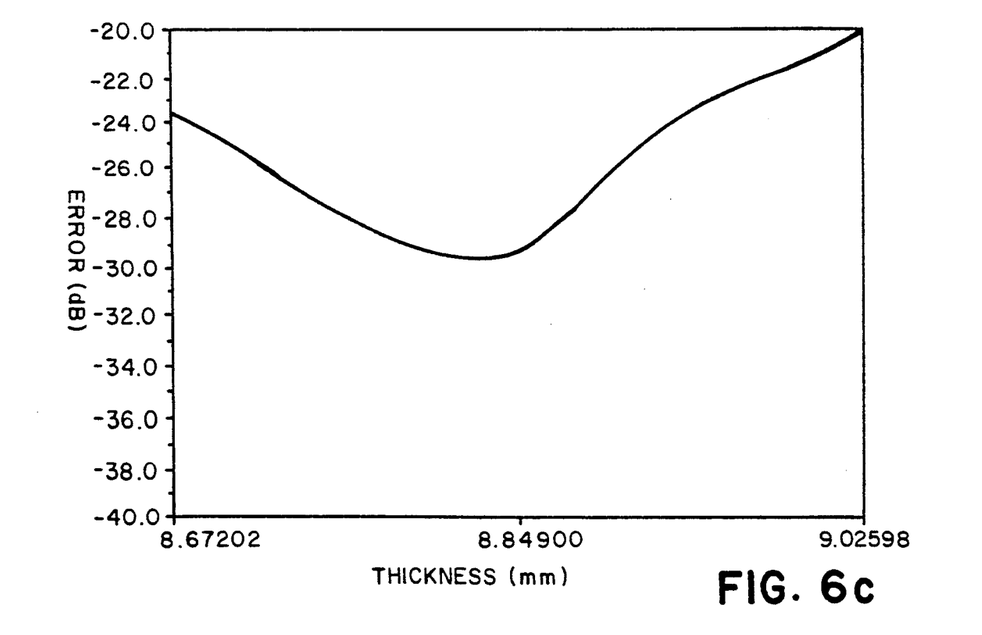
FIG. 6c is a graph of the error versus the assumed thicknesses of the casing which accompanied the fitting of the model to the return waveforms.
Figure 7:
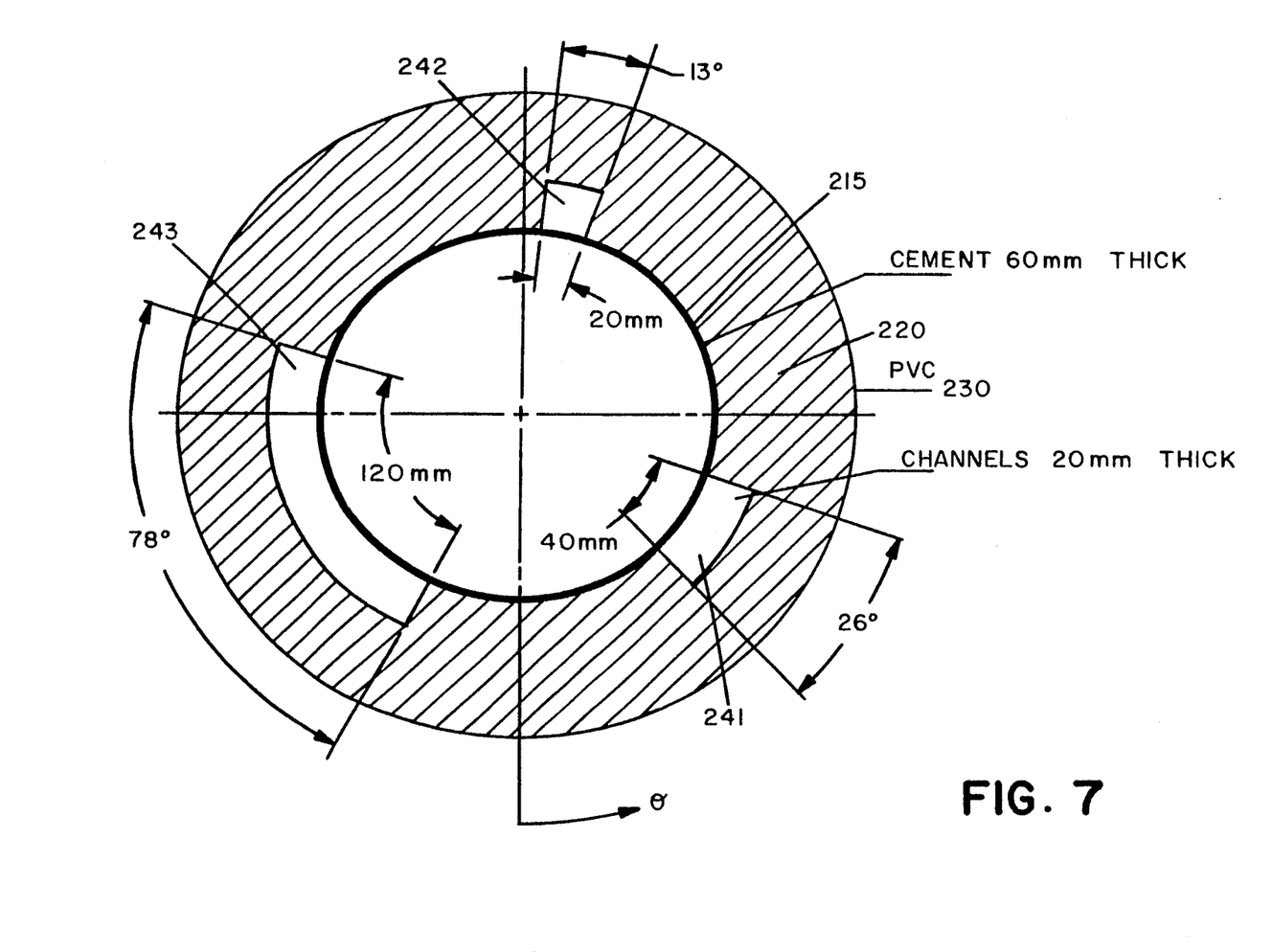
FIG. 7 is a cross-section of a cemented casing used in test experiments with a characterized transducer.

Using the effective standoff and effective radius characterizations obtained via FIGS. 6a–6c, the investigated casing 210 was cemented with 60 mm thick cement 220 held within a PVC pipe 230, as seen in FIG. 7. Three polystyrene foam filled 20 mm thick channels 241, 242, and 243 were spread around the circumference of the casing. The casing was scanned azimuthally in three degree increments yielding one hundred and twenty waveforms. The cement had a nominal impedance of 6.6 MRayl, while the polystyrene foam had an impedance approaching 0 MRayl.

Figure 8A:
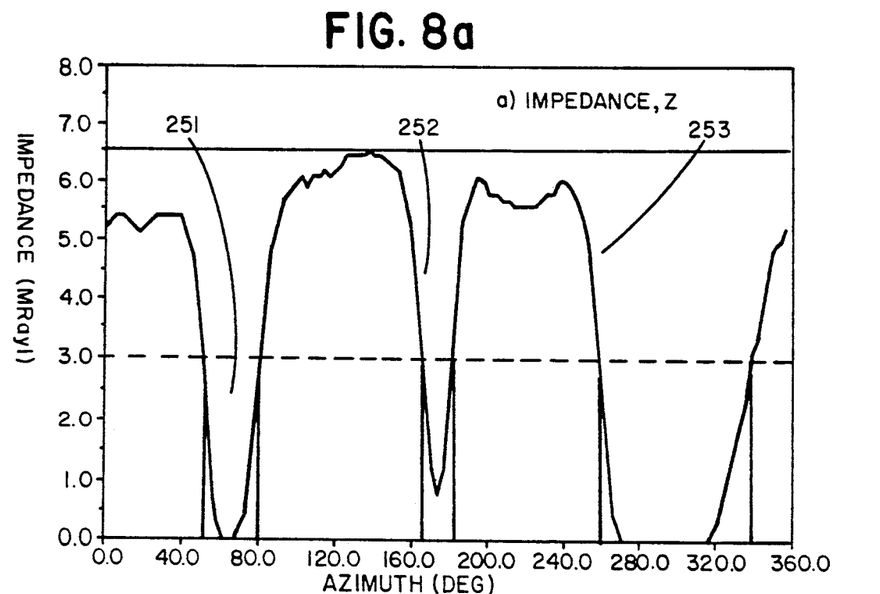
FIGS. 8a and 8b are graphs of the impedance measured by the characterized transducer in a test experiment utilizing the casing of FIG. 7, and the error found in fitting the model to the return waveform.
Figure 8B:
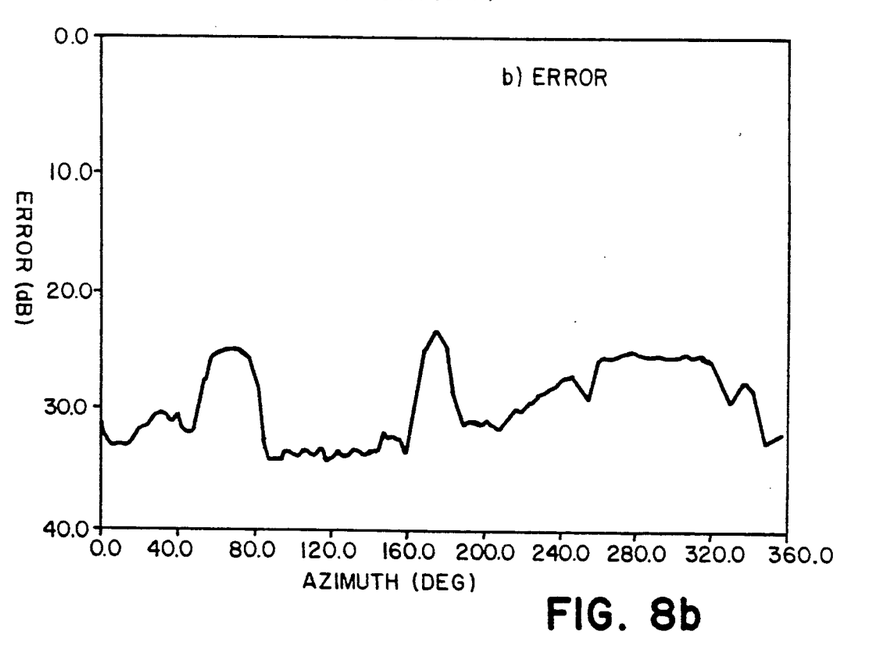

FIGS. 8a and 8b show the results of processing the scan data. FIG. 8a shows impedance verses the azimuth, and FIG. 8b shows the error in dB versus azimuth. With the typical assumption that impedances of less than 3.0 MRayl indicate fluids, and impedances of 3.0 MRayl or more indicate solids, it will be appreciated that the results of FIG. 8a are excellent. The first dip 251 in impedance in FIG. 6b shows impedance of less than 3.0 MRayl for about twenty-six degrees. The second dip 252 shows impedance of less than 3.0 MRayl for about thirteen degrees; while the third dip 253 shows impedance of less than 3.0 MRayl for about seventy-eight degrees. Not only does this agree perfectly with the arrangement of FIG. 5, but the relative locations of the dips also perfectly correspond. Further, a review of FIG. 8b indicates that the error ranged from approximately −23 dB to about 31 34 dB, which is indicative of an excellent fit throughout.

There have been described and illustrated herein methods for characterizing transducers and method utilizing characterized transducers for determining the cement impedance of a cased well. While particular embodiments have been described, it is not intended that the invention be limited thereto, as it is intended that the invention be as broad in scope as the art will allow. Thus, one skilled in the art will appreciate that the invention applies to characterization of acoustic transducers for any purpose whatsoever, and is not limited to the characterization of transducers for oil well applications. Further, with respect to oil well applications, while the use of a particular sonde or borehole tool in the cased well was described, those skilled in the art will appreciate that any of many tools could be utilized. Likewise, while the invention was described with reference to the transducer characterization as reducing parameters by limiting the Johnson-Devaney model to a Gaussin-apodized disk, those skilled in the art will appreciate that other types of transducers could be utilized in accord with the invention such as a piston type transducer, provided that parameters such as the effective radius and the effective standoff for that transducer are determined by fitting the inverse model to the test return signal (or a filtered version thereof). Also, while an auto-whitening filtering technique which corresponds to a bandpassed model was disclosed as being preferred for processing the return signal, it will be appreciated that other filtering could be utilized. What is required is that the filtered return signal correspond to the output of a model which can be solved in the inverse direction to find a kernel which is a function of the effective radius and the effective standoff. Similarly, while a least mean squared fitting technique was described as being preferred, those skilled in the art will appreciate that other techniques which find minimum error (i.e. "fitting techniques") could be utilized.

Those skilled in the art further appreciate that while downhole characterization is preferred for the cement impedance determination methods, uphole characterization in conjunction with downhole characterization or uphole characterization by itself can be utilized. Where uphole characterization is utilized in conjunction with downhole characterization, the uphole characterization can be used to find a range of expected effective radii and effective standoffs for the transducer. In this manner, computation relating to the downhole data can be reduced. Where uphole characterization is utilized by itself instead of characterizing downhole, a data base of effective radii and effective standoffs relating to different pressures, temperatures, casing thicknesses, and casing diameters must be generated uphole for a given transducer. The cement impedance measurement problem would then be solved by: obtaining the return signal, indications of the downhole pressure, temperature, casing diameter, and casing thickness; filtering the return signal appropriately; searching the data base for a, $S_e$, and $Z_{mud}$ at the appropriate pressure, temperature, casing diameter and casing thickness; and fitting model waveforms, with a, $S_e$, and $Z_{mud}$ fixed by the data base, and with cement impedance varying, to the filtered return signal so as to find the cement impedance which provides the best fit of the model to the filtered return signal. Thus, it will be appreciated by those skilled in the art that yet other charges and modifications to the disclosed embodiments can be made within the spirit and scope of the invention as so claimed.

I claim:

1. A method of characterizing an acoustic transducer, comprising:
   a) arranging said acoustic transducer a predetermined distance from a calibration target, wherein said calibration target is of known thickness, and said calibration target is in contact with matter of known impedance along its inner surface and outer surface;
   b) transmitting a pulse from said acoustic transducer toward said calibration target and measuring a return signal received therefrom; and
   c) fitting a return signal calculation generated by a model of said return signal to said return signal, said model having a limited number of parameters, to determine a value for at least one of said parameters and thereby characterizing said transducer, by substantially minimizing the difference between said return signal calculation and said measured return signal.

2. A method according to claim 1, wherein:
said limited number of parameters include at least one of radius and stand-off, and said acoustic transducer is characterized with a value for at least one of the effective radius and effective stand-off of said acoustic transducer as a function of said thickness of said calibration target.

3. A method according to claim 1, wherein:
said calibration target comprises one of a flat plate, a cylindrical tube, and a segment of a cylindrical tube.

4. A method according to claim 1, wherein:
said calculated return signal (V(f)) is defined according to $$V(f) = \int_0^{\pi/2} W(f,\theta) R(f,\theta|L) d\theta$$

wherein
W is the planewave kernel of a transducer parameterized by said limited number of parameters,
$\theta$ is the incidence angle of planewaves which can range over different angles,
f is frequency which can range over a frequency spectrum,
L are layers related to said calibration target, said matter along the inner surface of said target, and said matter along the outer surface of said target, and
$R(f,\theta|L)$ are reflection coefficients for the layers L, at frequency f, and incidence angle $\theta$.

5. A method according to claim 4, wherein:
said model of said return signal and said return signal are limited to a narrow frequency band substantially centered on a resonant frequency of said calibration target such that said planewave kernel is approximated to be substantially independent of frequency in said narrow frequency band.

6. A method according to claim 5, wherein:
said difference between said return signal calculation and said measured return signal is determined in said narrow frequency band.

7. A method according to claim 4, wherein:
said planewave kernel W is a planewave kernel for a Gaussian apodized disk transducer parameterized by its radius and standoff and said value includes values for at least one of the effective radius and effective stand-off of said acoustic transducer as a function of said thickness of said calibration target.

8. A method according to claim 7, wherein:
said model of said return signal and said return signal are limited to a narrow frequency band substantially centered on a resonant frequency of said calibration target such that
said planewave kernel is approximated to be substantially independent of frequency in said narrow frequency band.

9. A method according to claim 2, wherein:
said model of said return signal defines a calculated return signal V(f) according to $$V(f) = \int_0^{\pi/2} W(f,\theta) R(f,\theta|L) d\theta$$

wherein
W is the planewave kernel of a transducer parameterized by said limited number of parameters,
$\theta$ is the incidence angle of the planewave which can range over different angles,
f is a frequency which can range over a frequency spectrum,
L are layers related to said calibration target, said matter along the inner surface of said target, and said matter along the outer surface of said target, and
$R(f,\theta|L)$ are complex planar reflection coefficients for the layers L, at frequency f, and incidence angle $\theta$.

10. A method according to claim 9, wherein:
said model of said return signal and said return signal are limited to a narrow frequency band substantially centered on a resonant frequency of said calibration target such that said planewave kernel is approximated to be substantially independent of frequency in said narrow frequency band.

11. A method according to claim 6, wherein:
said difference between said return signal calculation and said measured return signal is determined utilizing a mean-squared error calculation.

12. A method according to claim 4, wherein:
said planewave kernel W is a planewave kernel for a Gaussian apodized disk transducer parameterized by its radius and standoff.

13. A method according to claim 12, wherein:
said model of said return signal and said return signal are limited to a narrow frequency band substantially centered on a resonant frequency of said calibration target such that
said planewave kernel is approximated to be substantially independent of frequency in said narrow frequency band.

14. A method according to claim 1, wherein:
said difference between said return signal calculation and said measured return signal is determined utilizing a means-squared error calculation.

15. A method according to claim 14, wherein:
in making said mean-squared error calculation, the error is computed over one or both of,
(i) a range of thicknesses in steps about the assumed thickness of said calibration target, and (ii) a range of time shifts in steps relative to said return signal, to substantially minimize the error.

16. A method according to claim 11, wherein:

in making said mean-squared error calculation, the error is computed over one or both of, (i) a range of thicknesses in steps about the assumed thickness of said calibration target, and (ii) a range of time shifts in steps relative to said return signal, to substantially minimize the error.

17. A method according to claim 1, further comprising:

in fitting said return calculation to said return signal and substantially minimizing said difference between said return signal calculation and said measured return signal, utilizing said difference as a quality indicator of the characterization of said acoustic transducer.

18. A method according to claim 17, wherein:

said difference between said return signal calculation and said measured return signal is determined utilizing a mean-squared error calculation, and said mean-squared error calculation of a best fit is said quality indicator.

19. A method according to claim 15, further comprising:

in fitting said return signal calculation to said return signal and minimizing said difference between said return signal calculation and said measured return signal in said narrow frequency band, utilizing said difference as a quality indicator of the characterization of said acoustic transducer.

20. A method according to claim 19, wherein:

said difference between said return signal calculation and said measured return signal is determined utilizing a mean-squared error calculation, and said mean-squared error calculation of a best fit is said quality indicator.

21. A method of measuring cement impedance of a cased well with a tool having an acoustic transducer, the casing of the well being of substantially known diameter, said method comprising:

a) characterizing said acoustic transducer by testing said acoustic transducer relative to a calibration target having a diameter substantially equal to the diameter of said casing of said well, and characterizing said acoustic transducer as having at least one of an effective radius ($a_e$), and an effective stand-off ($S_e$);

b) transmitting a pulse from said acoustic transducer toward said casing in said well and measuring a return signal received therefrom; and c) fitting a return signal calculation generated by a model of said return signal to said return signal to determine an indication of said cement impedance, by substantially minimizing the difference between said return signal calculation and said return signal, wherein said model of said return signal utilizes at least one of said effective radius and said effective stand-off of said acoustic transducer as determined during said characterizing step, and wherein said model of said return signal includes reflection coefficients which are a function of said cement impedance.

22. A method according to claim 21, wherein:

said tool includes said calibration target, and said characterizing step is accomplished downhole in said cased well.

23. A method according to claim 22, wherein:

said step of characterizing comprises 1) arranging said acoustic transducer a predetermined distance from said calibration target, wherein said calibration target is of known thickness, 2) transmitting a pulse from said acoustic transducer through borehole mud toward said calibration target and measuring the calibration return signal therefrom, and 3) fitting a return signal calculation generated by said model of said return signal to said calibration return signal by substantially minimizing the difference between said return signal and said calibration return signal, to determine at least one of said effective radius and said effective stand-off of said acoustic transducer as a function of said thickness of said calibration target.

24. A method according to claim 23, further comprising:

precharacterizing said tool uphole by testing said acoustic transducer uphole relative to an uphole calibration target, and precharacterizing said acoustic transducer as having an estimated effective radius and an estimated effective stand-off, wherein during said characterizing step, said estimated effective radius and said estimated effective stand-off are used in characterizing said acoustic transducer as having said effective radius and effective stand-off.

25. A method according to claim 21, wherein:

said step of characterizing comprises 1) arranging said acoustic transducer a predetermined distance from a calibration target, wherein said calibration target is located in a location other than in said well, said calibration target is of known thickness, and said calibration target is in contact with matter of known impedances along its inner and outer surfaces, 2) transmitting a pulse from said acoustic transducer through said matter in contact with said inner surface of said uphole calibration target toward said uphole calibration target and measuring a calibration return signal therefrom, and 3) fitting a return signal calculation generated by a model of said return signal to said calibration return signal by substantially minimizing the difference between said return signal calculation and said calibration return signal, to determine at least one of said effective radius and said effective stand-off of said acoustic transducer as a function of said thickness of said calibration target.

26. A method according to claim 21, wherein:

said calculated return signal (V(f)), used in step c) in determining an indication of cement impedance, is defined according to $$V(f) = \int_0^{\pi/2} W(f,\theta) R(f,\theta|L) d\theta$$

wherein wherein W is the planewave kernel of a transducer parameterized by a limited number of parameters, which planewave kernel is determined in said characterizing step, θ is the incidence angle of the planewave which can range over different angles, f is a frequency which can range over a frequency spectrum, L are layers related to said casing, and matter along the inner surface of said casing, and cement and/or other matter along the outer surface of said casing, and R(f,θ|L) are planar reflection coefficients for the layers L, at frequency f, and incidence angle θ, which planar reflection coefficients are functionally related to the impedance of said cement and/or other matter located along the outer surface of said casing.

27. A method according to claim 26, wherein:
said step c) of fitting a return signal calculation to determine an indication of cement impedance comprises, varying values of said planar reflection coefficients of said model and hence the results of said return signal calculations, and comparing said results of said return signal calculations with said return signal to substantially find a minimum difference, wherein said different values of planar reflection coefficients correspond to different cement impedances behind said casing.

28. A method according to claim 27, wherein:
said minimum difference between said return signal calculation and said measured return signal is determined utilizing a mean-squared error calculation.

29. A method according to claim 27, further comprising:
in fitting said return signal calculation to said return signal and substantially minimizing said difference between said return signal calculation and said measured return signal, utilizing said difference as a quality indicator of said cement impedance.

30. A method according to claim 23, wherein:
said calculated return signal (V(f)), used in step c) in determining an indication of cement impedance, and used in step a) 3) in determining at least one of an effective standoff and effective radius is defined according to $$V(f) = \int_0^{\pi/2} W(f,\theta)R(f,\theta|L)d\theta$$

wherein

W is the planewave kernel of a transducer parameterized by a limited number of parameters, the values for the parameters being varied to provide different planewave kernel values of fitting and minimizing in step a) 3), with the best fitting value being used in step c) in determining an indication of cement impedance, θ is the incidence angle of the planewave which can range over different angles, f is a frequency which can range over a frequency spectrum, L are layers related to said casing, and matter along the inner surface of said casing, and cement and/or other matter along the outer surface of said casing when used in step c), and relating to said calibration target, and said borehole mud when used in step a), and R(f,θ|L) are planar reflection coefficients for the layers L, at frequency f, and incidence angle θ, which planar reflection coefficients are predetermined when used in step a) 3), and which planar reflection coefficients are functionally related to the impedance of said cement and/or other matter located along the outer surface of said casing when used in step c).

31. A method according to claim 30, wherein:
said step c) of fitting a return signal calculation to determine an indication of cement impedance comprises, varying values of said planar reflection coefficients of said model and hence the results of said return signal calculations, and comparing said results of said return signal calculations with said return signal to find a substantially minimum difference, wherein said different values of planar reflection coefficients correspond to different cement impedances behind said casing.

32. A method according to claim 31, wherein:
said substantially minimum difference between said return signal calculation and said measured return signal is determined utilizing a mean-squared error calculation.

33. A method according to claim 31, further comprising:
in fitting said return signal calculation to said return signal and substantially minimizing said difference between said return signal calculation and said measured return signal, utilizing said difference as a quality indicator of said cement impedance.

34. A method according to claim 30, wherein:
said model of said return signal and said return signal are limited to a narrow frequency band substantially centered on a resonant frequency of said calibration target such that
said planewave kernel is approximated to be substantially independent of frequency in said narrow frequency band.

35. A method according to claim 33, wherein:
said transducer is a Gaussian apodized disk transducer, and said planewave kernel W is a planewave kernel for a Gaussian apodized disk transducer parameterized by its radius and standoff.

36. A method according to claim 35, wherein:
said model of said return signal and said return signal are limited to a narrow frequency band substantially centered on a resonant frequency of said calibration target such that
said planewave kernel is approximated to be substantially independent of frequency in said narrow frequency band.

37. A method according to claim 25, wherein:
said calculated return signal (V(f)), used in step c) in determining an indication of cement impedance, and used in step a) 3) in determining at least one of an effective standoff and effective radius is defined according to $$V(f) = \int_0^{\pi/2} W(f,\theta)R(f,\theta|L)d\theta$$

wherein

W is the planewave kernel of a transducer parameterized by a limited number of parameters, the values for the parameters being varied to provide different planewave kernel values of fitting and substantially minimizing in step a) 3), with the best fitting value being used in step c) in determining an indication of cement impedance, θ is the incidence angle of the planewave which can range over different angles, f is a frequency which can range over a frequency spectrum, L are layers related to said casing, and matter along the inner surface of said casing, and cement and/or other matter along the outer surface of said casing when used in step c), and relating to said calibration target, said matter in contact with the inner surface of said calibration target, and said matter in contact with the outer surface of said calibration target when used in step a), and $R(f,\theta|L)$ are planar reflection coefficients for the layers L, at frequency f, and incidence angle θ, which planar reflection coefficients are predetermined when used in step a) 3), and which planar reflection coefficients are functionally related to the impedance of said cement and/or other matter located along the outer surface of said casing when used in step c).

38. A method according to claim 37, wherein:

said step c) of fitting a return signal calculation to determine an indication of cement impedance comprises, varying values of said planar reflection coefficients of said model and hence the results of said return signal calculations, and comparing said results of said return signal calculations with said return signal to find a substantially minimum difference, wherein said different values of planar reflection coefficients correspond to different cement impedances behind said casing.

39. A method according to claim 38, wherein:

said substantially minimum difference between said return signal calculation and said measured return signal is determined utilizing a mean-squared error calculation.

40. A method according to claim 38, further comprising:

in fitting said return signal calculation to said return signal and minimizing said difference between said return signal calculation and said measured return signal, utilizing said difference as a quality indicator of said cement impedance.

41. A method according to claim 37, wherein:

said model of said return signal and said return signal are limited to a narrow frequency band substantially centered on a resonant frequency of said calibration target such that said planewave kernel is approximated to be substantially independent of frequency in said narrow frequency band.

42. A method according to claim 37, wherein:

said transducer is a Gaussian apodized disk transducer, and said planewave kernel W is a planewave kernel for a Gaussian apodized disk transducer parameterized by its radius and standoff.

43. A method according to claim 42, wherein:

said model of said return signal and said return signal are limited to a narrow frequency band substantially centered on a resonant frequency of said calibration target such that said planewave kernel is approximated to be substantially independent of frequency in said narrow frequency band.

44. A method of measuring the mud impedance of mud in a cased well with a tool having an acoustic transducer, the casing of the well being of substantially known diameter, said method comprising:

a) arranging said acoustic transducer a predetermined distance from a calibration target, wherein said calibration target is of known thickness, and said calibration target is in contact with matter of known impedance along its inner surface and outer surface;

b) transmitting a pulse from said acoustic transducer toward said calibration target and measuring a return signal received therefrom;

c) fitting return signal calculations generated by a return signal model to said first signal, said model having a limited number of parameters, to determine a value for at least one of said parameters, and thereby characterizing said transducer, by substantially minimizing the difference between said return signal calculation and said measured first return signal;

d) placing said tool in said mud in said well;

e) transmitting a pulse from said acoustic transducer through said mud toward a target in said well, said target in said well being of substantially the same thickness as said calibration target, and having said mud along at least one surface of said target, and measuring a second return signal received therefrom; and f) determining an indication of said mud impedance by minimizing the difference between said second return signal and additional return signal calculations generated by said model, wherein said additional return signals are a function of different mud impedances.

45. A method according to claim 4, wherein:

said return signal calculations and additional return signal calculations (V(f)) are defined according to $$V(f) = \int_0^{\pi/2} W(f,\theta) R(f,\theta|L) d\theta$$

wherein

W is the planewave kernel of a transducer parameterized by said limited number of parameters, θ is the incidence angle of the planewave which can range over different angles, f is a frequency which can range over a frequency spectrum, L are layers related to said calibration target and said matter along the inner surface of said target, and said matter along the outer surface of said target for step c), and are relate to said target in said well and said mud for step f), $R(f,\theta|L)$ are reflection coefficients for the layers L, at frequency f, and incidence angle θ.

46. A method according to claim 45, wherein:

said model of said return signal and said return signal are limited in a narrow frequency band substantially centered on a resonant frequency of said calibration target such that said planewave kernel is approximated to be substantially independent of frequency in said narrow frequency band.

47. A method according to claim 45, wherein:

said planewave kernel W is a planewave kernel for a Gaussian apodized disk transducer parameterized by its radius and standoff and said value include values for at least one of the effective radius and effective stand-off of said acoustic transducer as a function of said thickness of said calibration target.

48. A method according to claim 47, wherein:
said model of said return signal and said return signal are limited in a narrow frequency band substantially centered on a resonant frequency of said calibration target such that
said planewave kernel is approximated to be substantially independent of frequency in said narrow frequency band.

49. A method according to claim 44, comprising:
iteratively repeating steps c) and f), by using said mud impedance determination of step f) to change said return signal calculations of step c), and thereby adjusting said value for said parameter which characterizes said transducer, and using said adjusted value of said parameter to change said additional return signal calculations of step f), thereby adjusting mud impedance determination.

50. A method according to claim 25, further comprising:
generating a calibration database for said acoustic transducer by repeating said characterizing step for at least one of a plurality of different target parameters.

51. A method according to claim 50, wherein:
said different target parameters include calibration target thickness and calibration target radius.

52. A method according to claim 25, further comprising:
generating a calibration database for said acoustic transducer by repeating said characterizing step for at least one of a plurality of matter parameters.

53. A method according to claim 52, wherein:
said different matter parameters include matter pressure, matter temperature, and matter impedance.

54. A method according to claim 51, wherein:
said step of generating a calibration database further comprises repeating said characterizing step for at least one of a plurality of matter parameters including matter pressure, matter temperature, and matter impedance.

55. A method according to claim 32, wherein:
in making said mean-squared error calculation, the error is computed over one or both of,
(i) a range of thicknesses in steps about the assumed thickness of the casing of said well, and
(ii) a range of time shifts in steps relative to said return signal,
to substantially minimize the error.

56. A method according to claim 39, wherein:
in making said mean-squared error calculation, the error is computed over one or both of,
(i) a range of thicknesses in steps about the assumed thickness of the casing of said well, and
(ii) a range of time shifts in steps about the assumed time origin,
to substantially minimize the error.

57. A method according to claim 28, wherein:
in making said mean-squared error calculation, the error is computed over one or both of,
(i) a range of thicknesses in steps about the assumed thickness of the casing of said well, and
(ii) a range of time shifts in steps relative to said return signal,
to substantially minimize the error.

* * * * *